United States Patent [19]

Stahly et al.

[11] 4,370,278
[45] Jan. 25, 1983

[54] NUCLEOPHILIC SUBSTITUTION PROCESS

[75] Inventors: Barbara C. Stahly; G. P. Stahly, both of Baton Rouge, La.

[73] Assignee: Ethyl Corporation, Richmond, Va.

[21] Appl. No.: 317,321

[22] Filed: Nov. 2, 1981

[51] Int. Cl.$^3$ ............... C07C 121/78; C07C 121/66; C07C 53/132
[52] U.S. Cl. .................. 260/465 E; 260/465 G; 562/492
[58] Field of Search ............. 260/465 G, 465 E; 562/492

[56] References Cited

U.S. PATENT DOCUMENTS 3,755,427  8/1973  Adams et al. ............... 562/492
3,920,839  11/1975 Wasley ....................... 424/319
3,959,364  5/1976  Armitage et al. ........... 562/492
4,278,516  7/1981  Zaiko et al. ................. 204/158 HA

FOREIGN PATENT DOCUMENTS 45-28369  9/1970  Japan .

OTHER PUBLICATIONS

Golinski et al., Tetrahedron Letters, 37, pp. 3495–3498, (1978).
Makosza et al., J. Org. Chem., 45, 1534–1535, (1980).
Miyamatsu et al., J. of Medicinal Chem., vol. 17, 491–496, (1974).
Sunwell et al., J. of Medicinal Chem., vol. 18, 692–694, (1975).

*Primary Examiner*—Dolph H. Torrence
*Attorney, Agent, or Firm*—Donald L. Johnson; John F. Sieberth

[57] ABSTRACT

2-(Fluoronitrobenzene)alkyl cyanides are prepared by reacting a fluoronitrobenzene with an alpha-substituted alkyl cyanide in a substantially anhydrous aprotic solvent and in the presence of a base so that the alkyl cyanide reactant undergoes a nucleophilic substitution reaction on an unsubstituted carbon atom of the fluoronitrobenzene during which the alpha-substituent of the alkyl cyanide reactant functions as a leaving group. Use of 2-fluoronitrobenzene and an alpha-substituted propionitrile (e.g., 2-chloropropionitrile) produces a novel compound, 2-(3-fluoro-4-nitrobenzene)-propionitrile. Reduction of the nitro substituent produces another novel compound, 2-(4-amino-3-fluorobenzene)proprionitrile. This can readily be converted to 2-(3-fluoro-4-biphenylyl)propionitrile by means of a Gomberg-Bachmann reaction with an aromatic hydrocarbon or substituted aromatic hydrocarbon which in turn can be converted on hydrolysis into the corresponding 2-(2-fluoro-4-biphenylyl)propionic acid. Use of benzene in the Gomberg-Bachmann reaction thus enables production of flurbiprofen, a well-known pharmaceutical.

20 Claims, No Drawings

NUCLEOPHILIC SUBSTITUTION PROCESS

TECHNICAL FIELD

This invention relates to a process for the preparation of 2-(fluoronitrobenzene)alkyl cyanides, also known as 2-(fluoronitrobenzene) carboxylic acid nitriles. More particularly this invention relates to the production of 2-(3-fluoro-4-nitrobenzene)propionitrile and 2-(4-amino-3-fluorobenzene)propionitrile, novel compounds which are especially useful in the production of flurbiprofen by a new economical synthesis process.

BACKGROUND

The compound 2-(2-fluoro-4-biphenylyl)propionic acid—known as flurbiprofen—is a well known drug which possesses desirable anti-inflammatory, analgesic and anti-pyretic properties. Flurbiprofen and methods for its preparation are disclosed in U.S. Pat. Nos. 3,755,427 and 3,959,364. The former discloses a method for its preparation by reacting an ester of the appropriate substituted 4-biphenylyl acetic acid with diethyl carbonate to give a malonic ester, methylating the sodium derivative of this di-ester, hydrolyzing the di-ester, and then decarboxylating the resulting di-acid. The latter patent discloses a process for the preparation of aryl propionic acids—including flurbiprofen-13 by reacting a Grignard compound, obtained from an aryl bromide and magnesium, with a lithium, sodium, magnesium or calcium salt of 2-bromopropionic acid, followed by acidification. U.S. Pat. No. 4,278,516 discloses an improved synthesis process in which flurbiprofen can be prepared in a sequence of steps starting with 2-amino-4-methylbiphenyl.

THE INVENTION

A new process for the synthesis of flurbiprofen and related fluorobiphenylyl alkanoic acid derivatives has now been discovered in which these materials can be prepared in a simple and straightforward manner without need for tedious and time-consuming operations associated with conventional processes. In this new process 2-(fluoronitrobenzene)alkyl cyanides are produced in a novel synthesis reaction and used as intermediates in a reaction sequence in which, inter alia, 2-(aminofluorobenzene)alkyl cyanides are likewise produced and used as reaction intermediates.

This invention thus involves in one embodiment the discovery that 2-(fluoronitrobenzene)alkyl cyanides can be readily prepared in good yield with high selectivity by reacting a fluoronitrobenzene with an alpha-substituted alkyl cyanide in a substantially anhydrous aprotic solvent and in the presence of a base so that the alkyl cyanide reactant undergoes a nucleophilic substitution reaction on an unsubstituted carbon atom of the fluoronitrobenzene during which the alpha-substituent of the alkyl cyanide reactant functions as a leaving group.

In another embodiment of this invention 2-(aminofluorobenzene)alkyl cyanides are produced by forming a 2-(fluoronitrobenzene)alkyl cyanide in the above manner and then reducing the nitro substituent of the 2-(fluoronitrobenzene)alkyl cyanide to an amino substituent.

In still another embodiment 2-(fluorobiphenylyl)alkyl cyanides are formed by replacing the amino group of the 2-(aminofluorobenzene)alkyl cyanides by an aryl group, preferably by means of a Gomberg-Bachmann reaction.

A further embodiment involves converting the resultant 2-(fluorobiphenylyl)alkyl cyanides into the corresponding '-(fluorobiphenylyl) alkanoic acids.

Thus in a particularly preferred embodiment flurbiprofen is produced by (i) reacting 2-fluoronitrobenzene with an alpha-substituted propionitrile in a substantially anhydrous aprotic solvent and in the presence of a base so that the alpha-substituted propionitrile undergoes a nucleophilic substitution reaction on the unsubstituted carbon atom of the fluoronitrobenzene para to the nitro group during which the alpha-substituent of the propionitrile functions as a leaving group and 2-(3-fluoro-4-nitrobenzene)propionitrile is formed, (ii) reducing the nitro substituent of said 2-(3-fluoro-4-nitrobenzene)propionitrile to an amino substituent so that 2-(4-amino-3-fluorobenzene)propionitrile is formed, (iii) converting said 2-(4-amino-3-fluorobenzene)propionitrile into 2-(2-fluoro-4-biphenylyl)propionitrile preferably by means of a Gomberg-Bachmann reaction with benzene, and (iv) converting said 2-(2-fluoro-4-biphenylyl)propionitrile into 2-(2-fluoro-4-biphenylyl)propionic acid.

A variety of fluoronitrobenzenes can be used in the practice of this invention and thus use may be made of such compounds as 3-fluoronitrobenzene; 4-fluoronitrobezene; 2,3-difluoronitrobenzene; 2,4-difluoronitrobenzene; 2,5-difluoronitrobenzene; 2,6-difluoronitrobenzene; 3,4-difluoronitrobenzene; 3,5-difluoronitrobenzene as well as the various trifluoronitrobenzenes and tetrafluoronitrobenzenes preferably having an unsubstituted ortho or para position. Most preferably the para position relative to the nitro group of the fluoronitrobenzene reactant is unsubstituted as the nucleophilic substitution reaction of this invention tends to be highly selective on the para position and thereby produces 2-(fluoronitrobenzene)alkyl cyanides which are ideally suited for the synthesis of flurbiprofen and related fluorobiphenylyl alkanoic acid derivatives. A particularly preferred reactant is 2-fluoronitrobenzene which can be readily converted in good yield with high selectivity into flurbiprofen itself via the four-step reaction sequence described above.

Likewise, a variety of alpha-substituted alkyl cyanides may be used in practicing this invention. In general these alkyl cyanides which contain a leaving group, L, in the alpha-position may be represented by the formula:

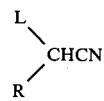

wherein R is hydrogen; a hydrocarbyl group (e.g., alkyl, alkenyl, alkynyl, cycloalkyl, cycloalkenyl, aryl, aralkyl, etc.) preferably containing up to about 10 carbon atoms; halogen, preferably bromine and most preferably chlorine; or a hydrocarbyloxyalkyl group. Exemplary leaving groups, L, include the following: alkoxy, cycloalkoxy, aryloxy, aralkoxy, haloalkoxy, halocycloalkoxy, haloaryloxy, haloaralkoxy, alkylthio, cycloalkylthio, arylthio, aralkylthio, haloalkylthio, halocycloalkylthio, haloarylthio, haloaralkylthio, and the like. Other suitable leaving groups have been referred to in the literature—see for example Tetrahedron Letters 37, 3495-8 (1978) and J. Org. Chem. 45, 1534-5

(1980). Since the leaving group does not remain in the resultant product it is preferable to employ an alkyl cyanide in which this alpha-substituent contains no more than about 10 carbon atoms although organic leaving groups having an even higher carbon content are deemed satisfactory. Preferred leaving groups are the halogens, viz., fluorine or iodine, preferably bromine and most preferably chlorine. Thus in accordance with one preferred embodiment of this invention the alkyl cyanide employed is a 2-haloalkyl cyanide, particularly a 2-chloroalkyl cyanide or a 2-bromoalkyl cyanide. A few exemplary materials of this type include 2-chloroacetonitrile, 2-chloropropionitrile, 2-chlorobutyronitrile, 2-chlorovaleronitrile, 2-bromoacetonitrile, 2-bromopropionitrile, 2-bromobutyronitrile, 2-iodoacetonitrile, 2-bromocapronitrile, 2-chloro-4-pentenenitrile, 2-bromo-3,3-dimethylbutanenitrile, 2-chloro-2-phenylacetonitrile, 2chloro-2-cyclohexylacetonitrile, 2-chloro-3-(3-chloro-o-tolyl)propionitrile, and 2-bromo-3-phenyl-propionitrile. Other suitable alpha-substituted alkyl cyanides include 2-methoxyacetonitrile, 2-butoxyacetonitrile, 2-phenoxyacetonitrile, 2-methylthioacetonitrile, 2-cyclohexylthioacetonitrile, 2-chloromethoxyacetonitrile, 2-(2-bromoethoxy)acetonitrile, 2-(4-fluorophenoxy)acetonitrile, and like compounds.

Use in the nucleophilic substitution process of 2,2-dihaloacetonitriles (R and L in the above formula are both halogen atoms), for example 2,2dibromoacetonitrile, is a desirable embodiment as it furnishes products having a reactive halogen atom in the alpha-position:

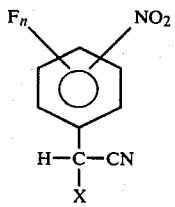

wherein X is halogen, preferably chlorine or bromine, and n is an integer of from 1 to 4. These products enable facile synthesis of a variety of useful end products. Most preferably the nitro group is in the para position relative to the halonitrile substituent, although it may be located in the ortho position.

Illustrative aprotic solvents which may be employed in the nucleophilic substitution reaction include ethers such as diethyl ether, dibutyl ether, 1-ethoxyhexane, tetrahydrofuran, 1,4-dioxane, 1,3-dioxolane, diglyme, 1,2-diethoxyethane, anisole, etc., and tertiary amines such as pyridine, N-ethylpiperidine, triethylamine, tributylamine, N,N-diphenyl-N-methyl amine, N,N-dimethylaniline, etc. Preferably dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile, and like materials are employed.

The bases for use in the nucleophilic substitution reaction are preferably organoalkali metal compounds and alkali metal hydrides such as butyl lithium, phenyl lithium, ethyl sodium, amyl sodium, butyl potassium, benzyl potassium, lithium hydride, sodium hydride, potassium hydride, and the like. Ordinarily use of sodium hydride or potassium hydride will be found most convenient and economical. Alternatively, use may be made of an alkali metal hydroxide (e.g., lithium hydroxide, sodium hydroxide, potassium hydroxide, etc.). If desired a phase transfer catalyst such as a quaternary ammonium halide or a suitable crown ether may be used along with the alkali metal hydroxide. In this instance the reaction medium preferably includes or consists of an inert liquid hydrocarbon such as hexane, heptane, isooctane, ligroin, toluene, xylene, or the like. When employing crown ethers in such phase transfer catalytic systems a 12-crown-4 ether should be used with lithium hydroxide, a 15-crown-5 ether should be used with sodium hydroxide, and an 18-crown-6 ether should be used with potassium hydroxide.

The nucleophilic substitution process of this invention is conducted in a substantially anhydrous reaction system and accordingly the components of the reaction system should be brought together and maintained under a dry inert atmosphere. Thus while it is possible to conduct this process in the presence of air, it is desirable to maintain the reaction system under an atmosphere of dry nitrogen or the like. Normally the nucleophilic substitution reaction itself is an exothermic reaction and thus its initiation can be readily ascertained by noting the exotherm produced. Ordinarily, therefore, the reactants are brought together in the reaction system at ambient temperatures although if desired the temperature may be raised or lowered to suit the needs of the occasion.

For best results it is desirable to employ an excess of the nitrile reactant relative to the fluoronitrobenzene reactant. It is, of course, possible to employ the fluoronitrobenzene in excess relative to the nitrile although this will mean that the quantity of the desired product that can be formed will be limited by the quantity of the nitrile used. Normally the reaction system will contain at least one molar equivalent of the base per mol of fluoronitrobenzene reactant and preferably the molar ratio of the base to the fluoronitrobenzene is 2 or more.

The mode of addition in the nucleophilic substitution process is not particularly critical. Accordingly, it is convenient to add the fluoronitrobenzene reactant to a mixture of the other materials, add the base to a mixture of the other materials, add the reactants to a mixture of the base and aprotic solvent, introduce all four ingredients simultaneously into the reaction zone, or the like. Reaction ordinarily proceeds very rapidly and thus long reaction times are not required. The reaction will usually be completed within a matter of minutes or a few hours at ambient temperatures.

Various known procedures may be used for reducing the nitro substituent of the 2-(fluoronitrobenzene)alkyl cyanides to an amino substituent. By way of example the reduction may be effected using iron powder and dilute acetic or hydrochloric acid, or by hydrogenation using a suitable catalyst such as platinum, nickel, or the like. Use of palladium-catalyzed hydrogenation is preferred. The conditions used for effecting such reductions are well known and reported in the literature. See for example March, Advanced Organic Chemistry (McGraw-Hill, New York, 1977) pp. 1125-1126 and references cited therein, all disclosures of which are incorporated herein by reference.

Any appropriate process step or steps may be used when replacing the amino group of the 2-(aminofluorobenzene) alkyl cyanide by an aryl group when forming the 2-(fluorobiphenylyl) alkyl cyanide. A particularly desirable process for effecting this replacment is the Gomberg-Bachmann reaction which involves formation of diaryl compounds from aryl diazonium salts and aromatic compounds. The details for performing the Gomberg-Bachmann reaction are set forth in the literature—see for example J. Am. Chem. Soc. 46, 2339 (1924); Organic Reactions 2, 224 (1944); Chem. Rev. 57, 77 (1957); March, Advanced Organic Chemistry (McGraw-Hill, New York, 1977), pp 653-654; J. Chem. Soc. D 1971, 411, and references cited therein, all disclosures of which are incorporated herein by reference. One particularly convienent procedure for performing the Gomberg-Bachmann reaction involves reacting the 2-(aminofluorobenzene) alkyl cyanide with approximately 1.5 equivalents of isoamylnitrite in an aromatic hydrocarbon or substituted aromatic hydrocarbon such as toluene, ethylbenzene, xylene, trimethylbenzene, tetrahydronaphthalene, isobutylbenzene, phenols (e.g., phenol, cresol, o-isopropylphenol, 4-hydroxyanisole, mono-, di- and tribromophenols, etc.), halobenzenes (e.g., mono-, di- and trifluorobenzenes, chlorobenzenes, bromobenzenes, chlorobromobenzenes, etc.), aromatic ethers (e.g., anisole, diphenylether, etc.), nitroaromatics (e.g., nitrobenzene, fluoronitrobenzene, etc.) and the like, at a suitable reaction temperature (usually an elevated temperature). When preparing flurbiprofen the aromatic hydrocarbon used in this process will of course be benzene.

A variety of well-known hydrolysis procedures can be used for converting the 2-(fluorobiphenylyl)alkyl cyanides into the corresponding 2-(fluorobiphenylyl) alkanoic acids. The hydrolysis is normally performed in the presence of water and a suitable polar organic solvent such as low-molecular weight alcohols (e.g., methanol or ethanol), 1,4-dioxane, acetone, low-molecular weight carboxylic acids (e.g., acetic acid or propionic acid), N-methylpyrrolidinone, dimethylsulfoxide, or the like. The hydrolysis may be performed in a neutral system, or recourse may be had to use of either basic or acidic hydrolysis. Reaction temperatures will usually fall between 0° C. and the boiling point of the reaction medium. These and other details of the hydrolysis reaction can be found in the literature—see for example March, Advanced Organic Chemistry (McGraw-Hill, New York, 1977) pp.809-810 and references cited therein, all disclosures of which are incorporated herein by reference.

The practice of this invention will be still further apparent from the following illustrative examples.

EXAMPLE I

Into a flame dried flask under nitrogen was placed 1.3 grams (0.026 mol) of NaH (50% dispersion in mineral oil). This was washed twice with 10 ml portions of petroleum ether (bp 35°-60° C.) and dried in a nitrogen stream. Then 25 ml of N,N-dimethylformamide (DMF; dried over 3 Angstrom molecular sieves) was added followed by dropwise addition (over 20 minutes) of a solution of 2.2 ml (0.021 mol) of 2-fluoronitrobenzene and 1.9 ml (0.023 mol) of 2-chloropropionitrile in 10 ml of DMF. The mixture became red and hot during the dropwise addition. A small portion of the reaction mixture was worked up by partitioning between 1 N HCl and diethyl ether, and analysis of the ether layer by gas chromatography (GC) indicated some starting material had not reacted. A second (0.40 g, 0.008 mol) and third (0.80 g, 0.017 mol) portion of 50% NaH were added so that workup of a reaction mixture sample followed by GC analysis indicated that no starting material remained. The reaction mixture was poured into 250 ml of 1 N HCl and extracted with six 200 ml portions of ether. The ether layers were combined, dried (MgSO$_4$), and concentrated to give a black oil which was adsorbed on 15 g of Silica Gel 60 (230-400 mesh) and loaded on a column of 150 g Silica Gel 60 packed in 40% CH$_2$Cl$_2$/60% petroleum ether (bp 35°-60° C.). Elution with the same solvent mixture afforded four fractions which, by GC area %, contain 1.8 g (44%) of 2-(3-fluoro-4-nitrobenzene)propionitrile. This compound was characterized by NMR, IR, and mass spectrometry.

EXAMPLE II

A slurry of 240 mg (5.0 mmols) of NaH (50% in mineral oil) in 2 ml of pyridine was treated dropwise, under nitrogen, with 0.26 ml (0.35 g, 2.5 mmols) of 2-fluoronitrobenzene followed by 0.22 ml (0.23 g, 2.6 mmols) of 2-chloropropionitrile. The purple reaction mixture was stirred at room temperature under nitrogen for 15 minutes, then was poured into an equal volume of 5% HCl and extracted with an equal volume of CH$_2$Cl$_2$. The organic phase was shown by gas chromatography-mass spectral analysis (GC-MS) to contain 2-(3-fluoro-4-nitrobenzene)propionitrile.

EXAMPLE III

A solution of 0.61 g (3.1 mmol) of 2-(3-fluoro-4-nitrobenzene)propionitrile in 10 ml of absolute ethanol was treated with 0.03 g of 7% palladium on carbon and hydrogenated at 45 psi of hydrogen (Parr apparatus) for 1 hour. The reaction mixture was filtered and concentrated to give 0.54 g of an oil which darkened on standing. A portion of this oil was purified on 1 mm silica gel plates (developed with CH$_2$Cl$_2$) to give 2-(4-amino-3-fluorobenzene)propionitrile, which was characterized by NMR, IR, and mass spectrometry.

EXAMPLE IV

A solution of 1.2 g (6.2 mmol) of 2-(3-fluoro-4-nitrobenzene)propionitrile in 24 ml of absolute ethanol was treated with 0.06 g of 7% palladium on carbon and hydrogenated at 40-45 psi hydrogen pressure (Parr apparatus) for 1 hour. The reaction mixture was filtered and the filtrate was shown to contain, by GC analysis (area percent) 99% 2-(4-amino-3-fluorobenzene)propionitrile. Removal of the solvent in a rotary evaporator gave 1.1 gram of a yellow oil which quickly darkened on standing.

EXAMPLE V

A solution of 25 mg (0.15 mmol) of 2-(4-amino-3-fluorobenzene)propionitrile, 0.2 ml of benzene, and 0.03 ml (0.25 mmol) of isoamyl nitrite was heated at reflux for 1.5 hours. GC analysis (area percent) of the reaction mixture indicated the presence of 25% unreacted starting material and 60% of a product which was identified by GC-MS to be 2-(2-fluoro-4-biphenylyl)propionitrile.

We claim:
1. A process for the preparation of 2-(fluoronitrobenzene)alkyl cyanides which comprises reacting a fluoronitrobenzene with an alpha-substituted alkyl cyanide in a substantially anhydrous aprotic solvent and in the presence of a base so that the alkyl cyanide reactant undergoes a nucleophilic substitution reaction on an unsubstituted carbon atom of the fluoronitrobenzene during which the alpha-substitutent of the alkyl cyanide reactant functions as a leaving group.

2. A process of claim 1 wherein the fluoronitrobenzene is unsubstituted in the position para to the nitro group.

3. A process of claim 1 wherein the base is an alkali metal hydride or an organoalkali metal compound, the aprotic solvent is a dipolar aprotic solvent, and the fluoronitrobenzene is a monofluoronitrobenzene.

4. A process of claim 3 wherein the base is sodium hydride or potassium hydride and the monofluoronitrobenzene is 2-fluoronitrobenzene.

5. A process of claim 1 wherein the alkyl cyanide is a 2-haloalkyl cyanide.

6. A process of claim 5 wherein the base is sodium hydride or potassium hydride, the fluoronitrobenzene is 2-fluoronitrobenzene and the 2-haloalkyl cyanide is 2-chloropropionitrile or 2-bromopropionitrile.

7. 2-(3-fluoro-4-nitrobenzene)propionitrile.

8. A process for the preparation of 2-(aminofluorobenzene)alkyl cyanides which comprises (i) reacting a fluoronitrobenzene with an alpha-substituted alkyl cyanide in a substantially anhydrous aprotic solvent and in the presence of a base so that the alkyl cyanide reactant undergoes a nucleophilic substitution reaction on an unsubstituted carbon atom of the fluoronitrobenzene during which the alpha-substituent of the alkyl cyanide reactant functions as a leaving group and a 2-(fluoronitrobenzene) alkyl cyanide is formed, and (ii) reducing the nitro substituent of said 2-(fluoronitrobenzene) alkyl cyanide to an amino substituent.

9. A process of claim 8 wherein the reduction of (ii) is effected by means of palladium-catalyzed hydrogenation.

10. A process of claim 8 wherein the alpha-substituted alkyl cyanide in (i) is a 2-halopropionitrile.

11. A process of claim 10 wherein in (i) the base is sodium hydride or potassium hydride, the fluoronitrobenzene is 2-fluoronitrobenzene and the 2-halopropionitrile is 2-chloropropionitrile or 2-bromopropionitrile.

12. 2-(4-Amino-3-fluorobenzene)propionitrile.

13. A process for the preparation of 2-fluorobiphenylyl)alkyl cyanides which comprises (i) reacting a fluoronitrobenzene with an alpha-substituted alkyl cyanide in a substantially anhydrous aprotic solvent and in the presence of a base so that the alpha-substituted alkyl cyanide reactant undergoes a nucleophilic substitution reaction on an unsubstituted carbon atom of the fluoronitrobenzene during which the alphasubstituent of the alkyl cyanide reactant functions as a leaving group and a 2(-fluoronitrobenzene) alkyl cyanide is formed, (ii) reducing the nitro substituent of said 2-(fluoronitrobenzene) alkyl cyanide to an amino substituent so that a 2-(aminofluorobenzene) alkyl cyanide is formed, and (iii) replacing the amino group of said 2-(aminofluorobenzene) alkyl cyanide by an aryl group so that a 2-(fluorobiphenylyl) alkyl cyanide is formed.

14. A process of claim 13 wherein (iii) is effected by means of a Gomberg-Bachmann reaction.

15. A process for the preparation of 2-(fluorobiphenylyl) propionic acids which comprises (i) reacting a fluoronitrobenzene with an alpha-substituted propionitrile in a substantially anhydrous aprotic solvent and in the presence of a base so that the alpha-substituted propionitrile undergoes a nucleophilic substitution reaction on an unsubstituted carbon atom of the fluoronitrobenzene during which the alpha-substituent of the propionitrile functions as a leaving group and a 2-(fluoronitrobenzene) propionitrile is formed, (ii) reducing the nitro substituent of said 2-(fluoronitrobenzene) propionitrile to an amino substituent so that a 2-(aminofluorobenzene) propionitrile is formed, (iii) converting said 2-(aminofluorobenzene) propionitrile into a 2-(fluorobiphenylyl) propionitrile by means of a Gomberg-Bachmann reaction, and (iv) converting said 2-(fluorobiphenylyl) propionitrile into the 2-(fluorobiphenylyl) propionic acid.

16. A process of claim 15 wherein (i) the fluoronitrobenzene is 2-fluoronitrobenzene and the alpha-substituted propionitrile is 2-chloropropionitrile or 2-bromopropionitrile.

17. A process of claim 15 wherein the Gomberg-Bachmann reaction is performed with benzene so that 2-(2-fluoro-4-biphenylyl)propionitrile is formed.

18. A process for the preparation of 2-(2-fluoro-4-biphenylyl)propionic acid which comprises (i) reacting 2-fluoronitrobenzene with an alpha-substituted propionitrile in a substantially anhydrous aprotic solvent and in the presence of a base so that the alpha-substituted propionitrile undergoes a nucleophilic substitution reaction on the unsubstituted carbon atom of the fluoronitrobenzene para to the nitro group during which the alpha-substituent of the propionitrile functions as a leaving group and 2-(3-fluoro-4-nitrobenzene) propionitrile is formed, (ii) reducing the nitro substituent of said 2-(3-fluoro-4-nitrobenzene)propionitrile to an amino substituent so that 2-(4-amino-3fluorobenzene)propionitrile is formed, (iii) converting said 2-(4-amino-3-fluorobenzene)propionitrile into 2-(2-fluoro-4-biphenylyl)propionitrile by means of a Gomberg-Bachmann reaction with benzene, and (iv) converting said 2-(2-fluoro-4-biphenylyl)propionitrile into 2-(2-fluoro-4-biphenylyl)propionic acid.

19. A process of claim 18 wherein in (i) the base is an alkali metal hydride or an organoalkali metal compound and the alpha-substituted propionitrile is 2-chloropropionitrile.

20. A process of claim 19 wherein in (i) the base is sodium hydride or potassium hydride and the aprotic solvent is a dipolar aprotic solvent.

* * * * *